United States Patent [19]
Shibata et al.

[11] Patent Number: 5,574,023
[45] Date of Patent: Nov. 12, 1996

[54] INTRAMOLECULARLY CROSSLINKED (1→3)-β-D-GLUCANS

[75] Inventors: Yuko Shibata; Jun Aketagawa; Shigenori Tanaka, all of Tokyo, Japan

[73] Assignee: Seikagaku Kogyo Kabushiki Kaisha (Seikagaku Corporation), Tokyo, Japan

[21] Appl. No.: 369,321

[22] Filed: Jan. 6, 1995

Related U.S. Application Data

[63] Continuation of Ser. No. 926,394, Aug. 10, 1992, abandoned.

[30] Foreign Application Priority Data

Aug. 8, 1991 [JP] Japan ................. 3-222451

[51] Int. Cl.$^6$ ............ A01N 43/04; A61K 31/715; C07G 3/00; C12P 19/04
[52] U.S. Cl. ............ 514/54; 435/101; 536/18.6
[58] Field of Search ............ 514/54; 536/18.6; 435/101

[56] References Cited

U.S. PATENT DOCUMENTS

| | | | |
|---|---|---|---|
| 4,835,265 | 5/1989 | Muzzarelli | 536/18.7 |
| 4,863,907 | 9/1989 | Sakurai et al. | 514/56 |

OTHER PUBLICATIONS

Jun Aketagawa et al "Activation of Limulus Coagulation Factor G by Several (1→3)-β-D-Glucans: Comparison of the Potency of Glucans with Identical Degree of Polymerization but Different Conformations" *J. Biochem.* 113:683–686 (1993).

Chibara, G., Yakugaku Zasshi, 108(3), 171–186 (1988).
Saito, H. et al., Macromolecules, 11(6), 1244–1251 (1978).
Morita, T. et al., FEBS Letters, 129(2), 318–321 (1981).
Ochiai, M. et al., J. Biol. Chem., 263(24), 12056–12062 (1988).
Czop, J. K. et al., J. Immunol., 141(9), 3170–3176 (1988).
Yanaki, T. et al., Agric. Biol. Chem., 50(9), 2415–2416 (1986).
Saito, H. et al., XVth International Carbohydrate Symposium; Aug. 12–17, p. 289 (1990).
Ohno, N. et al., Carbohydrate Research, 207, 311–318 (1990).
Saito, H. et al., Carbohydrate Research, 217, 181–190 (1991).
Tanaka, S. et al., Carbohydrate Research, 218, 167–174 (1991).

*Primary Examiner*—David M. Naff
*Assistant Examiner*—Deborah K. Ware
*Attorney, Agent, or Firm*—Sughrue, Mion, Zinn, Macpeak & Seas

[57] ABSTRACT

The invention stabilizes single helix conformation (1→3)-β-D-glucans by intramolecular crosslinking and provides (1→3)-β-D-glucans showing stable biological activities. Thus, intramolecularly crosslinked (1→3)-β-D-glucans having a stable single helix conformation are produced by introducing a functional group into hydroxyl groups of (1→3)-β-D-glucans, then causing the thus-obtained functional glucans to take a single helix conformation, and subjecting these, either as such or after binding them to a receptor therefor, to intramolecular crosslinking between the functional groups introduced, if necessary followed by releasing the receptor therefrom.

6 Claims, 1 Drawing Sheet

INTRAMOLECULARLY CROSSLINKED (1→3)-β-D-GLUCANS

This is a continuation of application Ser. No. 07/926,394 filed Aug. 10, 1992 (abandoned).

FIELD OF THE INVENTION

This invention relates to intramolecularly crosslinked (1→3)-β-D-glucans having a stable single helix conformation and, more particularly, to intramolecularly crosslinked (1→3)-β-D-glucans whose single helix conformation is stabilized by intramolecular crosslinking and which accordingly show stable biological activities and to a method of producing the same.

BACKGROUND OF THE INVENTION

Investigations in recent years have revealed that (1→3)-β-D-glucans have various biological activities. For instance, mention may be made of manifestation of host-mediated antitumor activity (activation of phagocytosis by macrophages, monocytes or the like, increase in bactericidal activity, etc.), activation of the mammalian alternative pathway of complement system, activation of factor G of horseshoe crab hemolymph coagulation system, and activation of the phenol oxidase system in arthropods, such as insects, and in mollusks, among others.

While the detailed mechanisms of the cell activation of (1→3)-β-D-glucans as mentioned above are not yet clear, it is considered that specific receptors sensitive to (1→3)-β-D-glucans exist on the cell surface and that when (1→3)-β-D-glucans are bound to said receptors, signals are transmitted therefrom to effectors by certain cellular mechanisms to thereby cause cell activation [Goro Chihara, Yakugaku Zasshi, 108 (3), 171–186 (1988)].

The higher-order structure of a (1→3)-β-D-glucan may vary depending on the environment in which said glucan is placed. So far known are the single helix, triple helix, random coil, and single-stranded structures. The single-stranded structure can exist only in anhydrous state. In certain instances, two or more of these higher-order structures may coexist. Carbohydrate chains with a polymerization degree of less than 20 cannot have such various higher-order structures [Saito, H. et al., Macromolecules, 11, 1244–1251 (1978)].

In the natural world, (1→3)-β-D-glucans occur as cell wall constituents of eumycetes in considerable amount. The occurrence of proteins sensitive to (1→3)-β-D-glucans as receptors therefor or as proenzymes in animal cells in charge of biophylaxis and required to recognize such glucans as foreign matters, for example in horseshoe crab amebocytes and immunocompetent cells such as mammalian leukocytes has been revealed and isolation of such proteins has been reported as well [Morita, T. et al., FEBS Letters, 129, 318–321 (1981); Ochiai, M. et al., J. Biol. Chem., 263, 12056–12062 (1988); Czop, J. P. et al., J. Immunol., 141, 3170–3176 (1988); and elsewhere].

Activation of cells sensitive to such (1→3)-β-D-glucans is induced by (1→3)-β-D-glucans or naturally occurring polysaccharides having such a structure within their molecule, or derivatives thereof. However, among these substances, some will not show such activating activity. So far, the cause of this difference has been explained in terms of the difference in degree of polymerization, branching or lack of branching within the molecule, the difference in state bound to other substances, and/or the difference in solubility in water, among others. On the other hand, a theory has been published according to which (1→3)-β-D-glucans having a triple helix cause the activation mentioned above [Yanaki, T. et al., Agric. Biol. Chem., 50, 2415–2416 (1986)].

The present inventors observed that Sonifilan [trademark; Kaken Pharmaceutical Co., Ltd.; medicament; schizophyllan made uniform in molecular weight and higher-order structure], which has a triple helix conformation in aqueous solution, hardly activates horseshoe crab factor G and further that treatment of the above-mentioned triple helix conformation schizophyllan with an alkali to increase the single helix conformation content leads to a marked increase in the above-mentioned factor G activating activity. They further found that various (1→3)-β-D-glucans having single helix conformation show a high activating effect on the above factor G and are also highly effective in causing regression of mouse sarcoma 180, hence have marked antitumor activity. In view of these findings, they concluded that the biological activities of (1→3)-β-D-glucans are related to their single helix conformation [Saito, H., Yoshioka, Y., Uehara, N., Aketagawa, J., Tanaka, S. and Shibata, Y., XVth International Carbohydrate Symposium, Aug. 12–17 (1990), p. 289].

In aqueous solution, this single helix conformation of (1→3)-β-D-glucans tends to transform into other conformations, typically a triple conformation, to bring about an equilibrium state. In particular, under high temperature and high concentration conditions, the single helix conformation is known to rapidly transform into a triple helix conformation [Kozo Ogawa, Hyomen, 12, 678–689 (1974)].

In an ordinary physiological environment, such change in higher-order structure is not so swift. For instance, when (1→3)-β-D-glucans are observed for their biological activity in terms of horseshoe crab factor G activating ability within a short period of time, no great changes in activity are found. However, where efficacy judgment requires several days to several weeks from the first day of administration, as in antitumor activity testing in sarcoma 180, the single helix conformation of (1→3)-β-D-glucans administered is considered to change into other higher-order structures and accordingly their biological activities decrease with time and/or the biological activities are lost during storage, leading to decreases in tumor inhibiting effect, as is often observed.

SUMMARY OF THE INVENTION

Accordingly it is an object of the invention to stabilize the single helix conformation of (1→3)-β-D-glucans and provide intramolecularly crosslinked (1→3)-β-D-glucans capable of retaining their biological activities, in particular antitumor activity, for a prolonged period of time.

The present inventors made intensive investigations in an attempt to accomplish the above object and, as a result, found that when the single helix conformation of (1→3)-β-D-glucans is stabilized by intramolecular crosslinking, (1→3)-β-D-glucans showing a stable biological activity can be obtained.

The (1→3)-β-D-glucans of the present invention are intramolecularly crosslinked (1→3)-β-D-glucans having a stable single helix conformation. More specifically, they are intramolecularly crosslinked (1→3)-β-D-glucans which can be obtained by introducing a functional group into hydroxyl groups of a (1→3)-β-D-glucan having at least 20 D-glucoside units, causing the same to have a single helix conformation, and subjecting the same, either as such or after its binding to a (1→3)-β-D-glucan receptor, to intramolecular crosslinking between the functional groups introduced in the presence of a crosslinking agent, followed, as necessary, by elimination of said receptor, and which have a stable single helix conformation and the following characteristics.

(a) They have a single helix conformation content of at least 20% as determined in a hydrated solid state.

(b) When they are stored in the form of an aqueous solution or suspension at 4° C. for one month, at least 50% of their single helix conformation is retained.

The present invention further relates to a method of producing such intramolecularly crosslinked (1→3)-β-D-glucans.

DETAILED DESCRIPTION OF THE INVENTION

The (1→3)-β-D-glucans to be used in the practice of the invention are glucans having, in the molecules, carbohydrate chains of β-1,3-glucoside bonds represented by the following formula (I) or derivatives thereof in which part of hydroxyl groups are substituted.

(I)

The above (1→3)-β-D-glucans are polyglucosides containing, within each of their molecules, at least one (1→3)-β-D-polyglucoside structure moiety comprising at least 20, preferably at least 180, more preferably at least 370, consecutively bound glucose units via β-1,3-glucoside bonds represented by formula (I).

They may contain, as a side chain, one or more carbohydrate chains of β-1,4-glucoside bonds represented by formula (II), or one or more carbohydrate chains of β-1,6-glucoside bonds represented by formula (III)

(II)

(III)

They may also contain one or more carbohydrate chains of glucoside bonds other than β-1,3-glucoside bonds such as β-1,4-glucoside bonds or β-1,6-glucoside bonds intervening in their main chain.

The hydroxyl groups of the (1→3)-β-D-glucans may be substituted, for etherification, with an alkyl group such as methyl, a carboxylalkyl group such as carboxymethyl or, for esterification, with an acyl group such as acetyl, a sulfonic acid group such as methanesulfonic acid or p-toluenesulfonic acid, or an inorganic acid group such as sulfuric acid, phosphoric acid or nitric acid.

Such derivatives of the (1→3)-β-D-glucans should have unsubstituted hydroxyl groups for introduction of functional groups described below.

The substituted derivative may be in the form of a salt with a metal ion such as sodium, potassium, barium or calcium, with an organic amine such as triethylamine, or with ammonium.

The (1→3)-β-D-glucans to be used in the practice of the invention are not particularly limited in their molecular weight provided that the above requirement is satisfied.

Such (1→3)-β-D-glucans may be naturally occurring ones or synthetic ones, or partial chemical modifications thereof. From the ready availability viewpoint, naturally occurring ones are preferred, however.

As typical examples of such (1→3)-β-D-glucans, there may be mentioned the following.

(1) Those which are composed exclusively of (1→3)-β-D-glucoside units and are linear: for example, (1→3)-β-D-glucans from bacteria of the genus Alcaligenes (e.g. curdlan), paramylon from flagellates, β-glucans from higher plant fibrous tissues, and callose extractable from higher plant sieve tubes; as well as D-glucose polymers contained in partial hydrolysates of such (1→3)-β-D-glucans or of laminarans from brown algae.

(2) Those which comprise (1→3)-β-D-glucoside units and (1→6)-β-D-glucoside units: for example, laminarans from brown algae of the generus Laminaria or Eisenia, chrysolaminarans from diatoms, pachyman from *Poria cocos*, glucans from Phytophthora cell walls, sclerotan from Scleotinia, schizophyllan from *Schizophyllum commune*, scleroglucans from Sclerotium, Corticium, Stromatinia or the like, lentinan from *Lentinus edodes* and β-glucans from yeast cell walls. This category includes not only linear ones but also branched ones having simple glucosyl branches and ones having a dendriform molecular structure.

(3) Those which comprise (1→3)-β-D-glucoside units and (1→4)-β-D-glucoside units: for example, lichenans from Cetraria, Usnea, Evernia, etc., and β-glucans contained in barley albumen.

(4) Those containing substituted β-D-glucoside units: for example, derivatives of the (1→3)-β-D-glucans mentioned above under (1) to (3) as prepared by modification of at least part of the hydroxyl groups of the carbohydrate chain with an alkyl group such as methyl, a hydroxyalkyl group such as hydroxymethyl, a carboxyalkyl group such as carboxymethyl, an acyl group such as acetyl, an acid group such as a sulfuric sulfonic (e.g., methanesulfonic, p-toluenesulfonic), nitric or phosphoric acid residue, or some other substituent. Of course, they should still contain, per molecule, at least one (1→3)-β-D-glucan structure moiety comprising at least 20 consecutive unmodified (1→3)-β-D-glycoside units bound together. The substituent introduction can be carried out by a per se known method.

Among the (1→3)-β-D-glucans listed above, some are commercially available and the commercial products, as such, can be used in the practice of the invention. When necessary, fractions containing the (1→3)-β-D-glucoside units mentioned above may be prepared from said products by partial carbohydrate chain degradation and/or fractionation and subjected to the method of the invention.

Such partial carbohydrate chain degradation or fractionation can be carried out by a per se known method. For instance, partial carbohydrate chain degradation can be effected by treatment with an acid or alkali, hydrolysis using β-glucanase, acetolysis, sound wave treatment or the like. Fractionation can be effected by fractional precipitation using an organic solvent such as ethanol, acetone or diethyl ether, or a salt, or by using a moelcular sieve agent or a molecular sieve membrane.

In accordance with the invention, the intramolecularly crosslinked (1→3)-β-D-glucans having a stable single helix conformation are prepared by subjecting the (1→3)-β-D-glucans such as mentioned above, in a single helix conformation form, to intramolecular crosslinking.

The intramolecular crosslinking occurs between functional group-substituted hydroxyl groups in positions which allow the (1→3)-β-D-glucans to maintain their single helix conformation in the presence of a crosslinking agent having at least two functional groups. As examples of the functional group, there may be mentioned oxirane ring, amino, hydrazino, aldehyde and carboxymethyl groups. Among these, amino, hydrazino, aldehyde and carboxymethyl groups are preferred and hydrazino and aldehyde groups are particularly preferred. Crosslinks are formed, for example, by reacting the above-mentioned functional groups with a crosslinking agent containing a spacer group such as hydrocarbon or hydroxyhydrocarbon chains having, at both ends thereof, functional groups such as amino, hydrazino, aldehyde or carboxyl groups that are reactive with counterpart functional groups such as mentioned above. The number of crosslink chain atoms between oxygen atoms of the hydroxyl groups at both ends is preferably 10 to 50, more preferably 15 to 25, as is estimable from FIG. 1.

In the practice of the invention, the crosslink formation is carried out in the following manner. The two steps involved may be carried out simultaneously.

(1) Functional group introduction

First, a functional group or a side chain containing the same is introduced into a (1→3)-β-D-glucan. Thus, the oxirane or amino, hydrazino, aldehyde or carboxymethyl group is introduced into part of hydroxyl groups occurring in the glucan by any of the reactions mentioned below.

1) Epoxidation with an oxirane compound. The oxirane compound to be used is, for example, an epihalohydrin such as epichlorohydrin, or a dioxirane compound such as diglycidyl ether.

2) Amination of the epoxy compound obtained in 1) with concentrated ammonia water.

3) Conversion of the epoxy compound mentioned above in 1) to the corresponding hydrazino compound by reaction with hydrazine hydrate or any of various dihyrazides. Hydrazine hydrate is used in the main. The dihydrazide may be of a short carbon chain. In some instances where a long crosslinking chain is desired, adipodihydrazide may be used to give long side chains.

4) Aldehyde group introduction into the hydrazino compound obtained in 3) using a dialdehyde and a reducing agent. The dialdehyde is, for example, glyoxal, malondialdehyde, succindialdehyde, glutardialdehyde or adipodialdehyde. One having a short carbon chain, such as glutardialdehyde, is preferably used. The reducing agent is, for example, sodium cyanoborohydride, sodium borohydride, dimethylamine-borane or trimethylamine-borane.

5) Oxidation of a glucosyl side chain bound to the 6-position of a glucose residue in the main chain of a scleroglucan such as schizophyllan, to give an aldehyde. Periodic acid, for instance, is used as the oxidizing agent.

6) Hydrazide formation of the aldehyde compound obtained in 5) with hydrazine hydrate or a dihydrazide. The hydrazino group introducing agent to be used is the same as mentioned in 3).

7) Carboxymethylation of a (1→3)-β-D-glucan. The carboxymethylating agent is, for example, monochloroacetic acid.

The reactions mentioned above may be carried out each in a per se known method. Such functional group introduction is performed so that the degree of substitution per three hydroxyl groups of one glucose residue in the (1→3)-β-D-glucan generally falls within the range of 0.1 to 1.0, preferably 0.4 to 0.8.

When a (1→3)-β-D-glucan in which at least part of its hydroxyl groups is/are substituted with a functional group such as mentioned above, for example carboxymethyl, is used as the starting material, the above functional group introduction step may be omitted.

(2) Formation of single helix conformation

After functional group introduction, the (1→3)-β-D-glucan is caused to have a single helix conformation depending on the higher order structure state thereof in the following manner. Even when the (1→3)-β-D-glucan that is available mostly has a single helix conformation, the same treatment should be carried out to increase the single helix conformation content since the single helix conformation tends to shift into a triple helix conformation during storage.

(1→3)-β-D-Glucans of single-stranded structure are converted to their single helix conformation by hydration.

(1→3)-β-D-Glucans with a triple helix conformation are converted to their single helix conformation by one of the following treatments.

1) They are dissolved in an alkaline solvent such as aqueous sodium hydroxide having a concentration of 0.3M or more and the solutions are maintained at pH 12 or above for a short period and then neutralized. To avoid cleavage of β-1,3-glucoside bonds by the alkali, the treatment is conducted at a temperature as low as possible, namely at 10° C. or below, preferably 0°–4° C. A treatment time of 30 seconds is sufficient while a treatment time longer than 1 hour is undesirable.

In cases where the system in the functional group introduction step is made alkaline, it is possible to obtain a single helix conformation by eliminating the alkali from said system by merely washing the same with water or neutralizing the same.

2) After addition of an acid, they are maintained at pH 1.5 or below for 15–60 minutes, followed by neutralization. The treatment temperature is preferably 0°–50° C., more preferably 20°–40° C.

3) Solid sample are dissolved in 100% dimethyl sulfoxide (hereinafter, DMSO) and the solutions are lyophilized and then hydrated in contact with water. Alternatively, the DMSO solutions obtained are dialyzed against distilled water.

(3) Receptor binding

The thus-obtained (1→3)-β-D-glucans with a single helix conformation may be subjected, as such, to crosslinking for the protection of their single helix conformation. More efficiently, however, they are bound to a (1→3)-β-D-glucan receptor under physiological conditions for binding site protection. As such receptor, there may be mentioned, for example, horseshoe crab amebocyte lysate or factor G thereof, arthropod phenol oxidase precursor, zymosan receptor on human lymphocyte and, further, carbohydrate-receptive amino acids such as tryptophan and N-acetyltryptophan, and triptophan-containing peptides.

The binding of a receptor and a (1→3)-β-D-glucan derivative is effected in a physiological environment to stabilize the receptor, for example in water or an aqueous salt solution.

(4) Inhibition of crosslinking between molecular chains

Then, a substance which is water-soluble but will not react with the functional group introduced in (1) is added to the aqueous solution obtained in (3) for the purpose of preventing crosslinking between molecular chains in the next intramolecular crosslinking step. As such water-soluble substance, there may be mentioned polyethylene glycol, polyvinyl alcohol, polyvinylpyrrolidone and the like as well as water-soluble copolymers containing these as principal constituents. In each step as described above, the reaction conditions varies depending on the reaction and the reactants. However, one skilled in the art could easily determine suitable reaction conditions from the known techniques and preparative experiments. Polyethylene glycol preferably has an average molecular weight of 20,000–500,000.

Such water-soluble substance is used preferably in an amount of 1–100 parts by weight, more preferably 10–50 parts by weight, per part by weight of the (1→3)-β-D-glucan.

Alternatively, instead of adding such water-soluble substance, a large amount of water may be added to thereby lower the (1→3)-β-D-glucan concentration in the system to an extreme extent, for example to $10^{-3}$ to $10^{-5}$ weight percent.

The addition of such water-soluble substance may be carried out in the next step (5) by adding the same in the form of an aqueous solution containing the crosslinking agent to be used in step (5) and the water-soluble substance.

(5) Intramolecular crosslinking

Using a bifunctional crosslinking agent reactive with the functional groups introduced in (1) or the functional groups occurring in the above-mentioned substituted (1→3)-β-D-glucan to be used as the starting material, intramolecular crosslinking is effected between the functional groups.

Thus, crosslinking is carried out using a crosslinking agent selected depending on the functional groups bound to the (1→3)-β-D-glucan, for example a diamine for the oxirane introduced in (1)-1, a dialdehyde plus a reducing agent, or a dibasic carboxylic acid or a salt thereof for the amino or hydrazino groups introduced in (1)-2, 3 or 6), a diamine or dihydrazide plus a reducing agent for the aldehyde groups introduced in (1)-4) or 5), or a diamine or dihydrazide plus a condensing agent for the carboxymethyl groups introduced in (1)-7). The crosslinking agent is not limited to those mentioned above, however.

Figure 1:
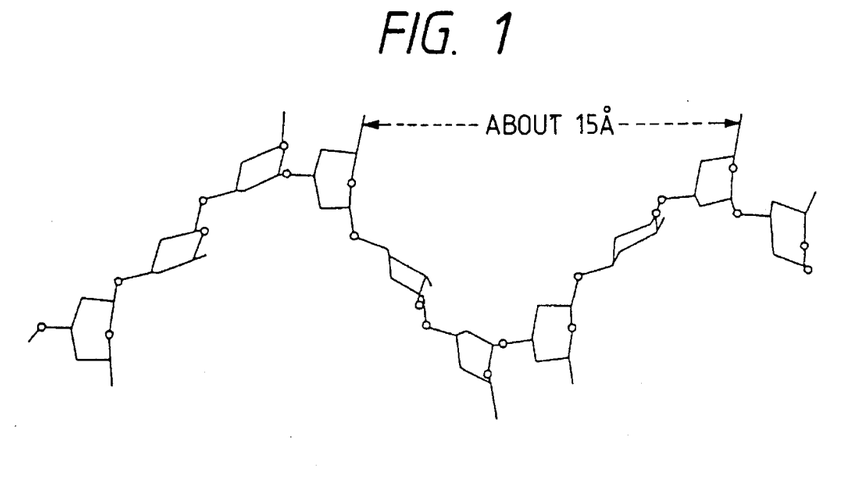
FIG. 1 schematically illustrates the single helix conformation of a (1→3)-β-D-glucan and the distance necessary for intramolecular crosslinking.

In the steric structure of (1→3)-β-D-glucans with a single helix conformation, the distance between $C_6$-hydroxyl groups of the corresponding glucose residue after one pitch of the helix is considered to be about 15 angstroms, as shown in FIG. 1. However, this helical conformation is flexible and, in the case of schizophyllan, for instance, the distance between the side 6-O-glucosyls occurring in a frequency of one per three glucose residues of the (1→3)-β-D-glucan main chain is about 15–20 angstroms. Therefore, a bifunctional compound having a molecular length suited for intramolecular crosslinking between a certain pair of functional groups which can stabilize such single helix conformation is preferable as the crosslinking agent. More specifically, the crosslinking agent is preferably selected such that the number of atoms involved in the crosslink between those hydroxyl groups of the glucose residues that are involved in crosslinking becomes 10–50, more preferably 15–25.

The diamine to be used as the crosslinking agent includes pentamethylenediamine, hexamethylenediamine, octamethylenediamine, nonamethylenediamine, decamethylenediamine, dodecamethylenediamine, etc., the dihydrazide includes adipodihydrazide, pentamethylenedihydrazide, hexamethylenedihyrazide, octamethylenedihydrazide, decamethylenedihydrazide, dodecamethylenedihydrazide, etc., the dialdehyde includes glutardialdehyde, adipodialdehyde, pimelic dialdehyde, hexamethylenedialdehyde, octamethylenedialdehyde, decamethylenedialdehyde, dodecamethylenedialdehyde, etc., and the dibasic carboxylic acid or salt thereof includes glutaric acid, adipic acid, pimelic acid, suberic acid, azelaic acid, sebacic acid, decamethylenedicarboxylic acid, brassilic acid, dodecamethylenedicarboxylic acid, etc., and salts thereof.

When a less water-soluble glucan, such as a high-molecular-weight (1→3)-β-D-glucan, is to be crosslinked, a crosslinking agent containing at least one hydroxyl group within the molecule can be successfully used to render the intramolecularly crosslinked (1→3)-β-D-glucan more water-soluble or hydrophilic. As such crosslinking agent, there may be mentioned 2,3,4-trihydroxyadipodihydrazide and 2,3,4-trihydroxyadipodialdehyde, among others.

The reducing agent to be used in combination with the crosslinking agent is, for example, sodium cyanoborohydride, sodium borohydride, dimethylamine-borane or trimethylamine-borane.

When a dibasic carboxylic acid or a salt thereof is used as the crosslinking agent between amino groups or hydrazino groups or when a diamine or dihydrazide is used as the crosslinking agent between carboxymethyl groups, it is desirable to combinedly use a condensing agent such as a carbodiimide reagent or N-ethoxy-carbonyl-2-ethoxy-1,2-dihydroquinoline (EEDQ), which react with the carboxy groups and promote the crosslinking. The carbodiimide reagent to be used is a water-soluble carbodiimde such as 1-ethyl-3-(3-di-methylaminopropyl)carbodiimide, cyclohexyl-3-(2-morpholinoethy)carbodiimde-meso-p-toluenesulfonate or dicyclohexylcarbodiimide.

(6) Receptor elimination

Generally, the receptor bound in (3) can be eliminated simultaneously in the separation step (7) by adding ethanol or acetone.

In some instances, however, addition of such solvent fails to cause receptor release. In such cases, prior to the separation step (7), the salt concentration is adjusted. For instance, the salt concentration in the system is adjusted to 0.5–5M by adding sodium chloride, magnesium chloride, sodium acetate or the like, whereby the receptor is released and can be recovered using an adsorbent or the like. In case the dissociation is still difficult to occur under these conditions, an acid (e.g., hydrochloric acid) or alkali (e.g., sodium hydroxide) having a concentration of 0.01–0.05N is added in a small amount to promote the dissociation.

It is also possible to use an ion exchange resin (anion exchange or cation exchange resin) for receptor release and adsorption.

(7) Separation

After receptor release, an appropriate solvent is added to the system containing the intramolecularly crosslinked (1→3)-β-D-glucan to cause precipitation of the same, whereby said glucan can be separated from the water, salt, and water-soluble substance added in (4), in the system. The solvent to be added is, for example, ethanol or acetone.

(8) Treatment of unreacted functional groups

The functional groups remaining uninvolved in the intramolecular crosslinking reaction in (5) are blocked by reacting an appropriate protecting group therewith. Thus, when the functional groups are amino or hydrazino groups, they are N-acetylated, for example with acetic anhydride in 0.1M sodium acetate. In the case of oxiranes, they are also acetylated with acetic anhydride. Aldehyde groups are aminoalkylated using ethanolamine, tris(hydroxymethyl)aminomethane or the like. Then, after thorough washing with an alkaline aqueous solution such as 0.1M sodium hydroxide, the intramolecularly crosslinked (1→3)-β-D-glucan is recovered by reprecipitation in the same manner as in (7).

Figure 2:
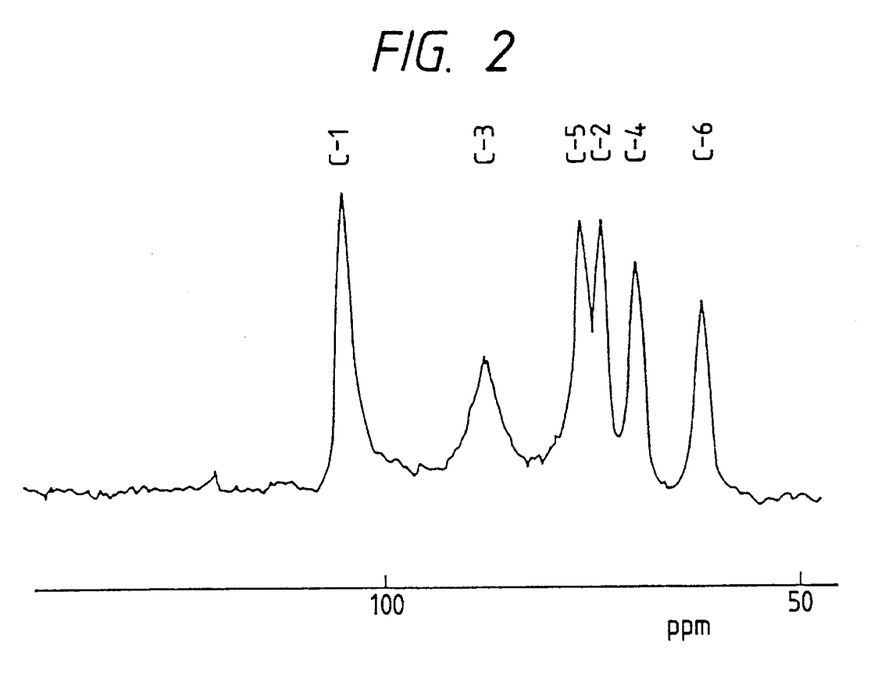
FIG. 2 shows a solid-state $^{13}C$ nuclear magnetic resonance ($^{13}C$-NMR) spectrum of single helix conformation curdlan.

When subjected to high-resolution $^{13}$C nuclear magnetic resonance (hereinafter, $^{13}$C-NMR) spectrometry, hydrated solid samples of the thus-obtained intramolecularly crosslinked (1→3)-β-D-glucans obtained in Example 2 gave C-2, C-3 and C-5 chemical shift values within the respective ranges of 73.0–73.8, 87.3–91.0, 75.6–75.8 ppm. Comparison of these with the chemical shift values (Table 1) in the $^{13}$C-NMR spectra for glucans each having the 100% single helix conformation (FIG. 2), 100% triple helix conformation and 100% random coil conformation revealed that said glucans contained a single helix conformation in their higher order structure.

The intramolecularly crosslinked (1→3)-β-D-glucans of the invention retain at least 50% of their single helix conformation even after one-month storage in aqueous solution or suspension at 4° C. This, hand in hand with the good retention of factor G activating ability and tumor inhibition rate, indicates that their single helix conformation is stable.

Such intramolecularly crosslinked (1→3)-β-D-glucans is useful as a drug for treating or preventing various diseases, for example tumor, of mammals including human. Particularly, they exhibit excellent growth-inhibiting effect against solid tumor, which have been regarded as being difficult to treat, and this effect lasts stably.

The pharmaceutical composition containing the crosslinked (1→3)-β-D-glucan can be administered to a patient parenterally (e.g. intravenous, intramuscular or subcutaneous injection), percutaneously or per rectum.

The crosslinked (1→3)-β-D-glucans may be formulated into an appropriate dosage form such as a liquid composition (e.g. aqueous solution, suspension), a solid composition or a semisolid composition, together with pharmaceutically acceptable carriers by a conventional method. The crosslinked (1→3)-β-D-glucans may also be formulated into a sustained release composition using a known technique.

The liquid composition such as an injectable solution can be prepared by dissolving or dispersing the crosslinked (1→3)-β-D-glucans in distilled water for injection, if required, together with a pH adjusting agent such as hydrochloric acid, sodium hydroxide, lactic acid, sodium lactate, disodium hydrogenphosphate, sodium dihydrogenphosphate and the like, an agent for making the composition isotonic such as sodium chloride, glucose and the like. The resulting solution or suspension may be filter sterilized followed by distribution into ampoules, or may be further mixed with mannitol, dextrin, cyclodextrin, gelatin and the like and freeze-dried in a vacuum. The freeze-dried product can be dissolved in an appropriate solution for injection upon use. Alternatively, the crosslinked (1→3)-β-D-glucans may be emulsified using an emulsifier such as lecithin, polyoxyethylene hydrogenated castor oil and the like to obtain an oil-in-water emulsion for injection.

The pharmaceutical composition for rectal infusion can be prepared by mixing the crosslinked (1→3)-β-D-glucan with a substrate for suppository such as tri-, di- or monoglyceride of cacao fatty acid, polyethylene glycol and the like, melting the mixture by heating and molding it under cooling. In another method, the crosslinked (1→3)-β-D-glucan may be dissolved or suspended in polyethylene glycol, soy bean oil and the like and coated with a gelatin membrane.

The dose, which is sufficient to effectively inhibit the target tumor, may vary depending on the kind of animal to be treated, symptom, route of administration and dosage form. These substances have very low toxicity and show no adverse effects upon administration.

The following working and test example illustrate the invention in further detail but are by no means limitative of the scope of the invention.

EXAMPLE 1

Glutardialdehyde-crosslinked hydrazinocurdlan (no receptor added)

Curdlan of a commercial grade (Wake Pure Chemical Industries) was thoroughly washed with water and the solvent was removed by suction filtration, whereby oligosaccharides and other impurities were removed. To 5 g of the thus-purified curdlan were added 30 ml of water, 13 ml of 2M aqueous sodium hydroxide and 3 ml of epichlorohydrin, in that order, with stirring. The mixture was stirred at 40° C. for 30 minutes for effecting the reaction, and the solid matter was thoroughly washed with an acetone (80%)-water (20%) mixture to give an epoxy compound. This was suspended in a half volume of water. To this suspension was added an equal volume of 80% hydrazine hydrate. The reaction was carried out at 40° C. for 1 hour with stirring, and the product was thoroughly washed with the same acetone-water mixture as mentioned above, dried, dissolved in DMSO to a concentration of 5% and lyophilized.

A solution of 2 g of polyethylene glycol with an average molecular weight of 50,000 in 10 ml of water was added to 1 ml of a 25% aqueous solution of glutardialdehyde to give a uniform aqueous solution. To this was added 1 g of the lyophilized curdlan mentioned above with hydrazino groups introduced therein. Then, 0.82 g of sodium cyanoborohydride was added and the intramolecular crosslinking reaction was effected by continuously stirring the mixture at 40° C. for 4 hours. Thereafter, ethanol was added to a concentration of 70%, and the mixture was allowed to stand for precipitation of crosslinked curdlan. The precipitate was collected by filtration and thoroughly washed with ethanol.

The thus-obtained intramolecularly crosslinked curdlan with a single helix conformation was suspended in 0.5 ml of 0.2M aqueous sodium acetate, 0.25 ml of acetic anhydride was added, the mixture was stirred for 30 minutes with cooling at 0° C., 0.25 ml of acetic anhydride was further added, and the mixture was continuedly stirred at room temperature for 30 minutes. In this way, unreacted amino groups were acetylated. The reaction product was washed with water and further thoroughly washed with 0.1M aqueous sodium hydroxide and water, then recovered by filtration and dried to give intramolecularly crosslinked curdlan of the invention with a single helix conformation.

EXAMPLE 2

Glutardialdehyde-crosslinked hydrazinocurdlan

Lyophilized hydrazinocurdlan was prepared in the same manner as in Example 1. To 1 g of the lyophilized curdlan with hydrazino groups thus introduced therein was added 1.0 ml of phosphate-buffered physiological saline containing 3 μg/ml of a horseshoe crab amebocyte lysate factor G fraction prepared in advance. The mixture was stirred until it became homogeneous and then allowed to stand at room temperature for 30 minutes.

A solution of 2 g of polyethylene glycol with an average molecular weight of 50,000 in 10 ml of water was added to 1 ml of a 25% aqueous solution of glutardialdehyde to give a uniform aqueous solution. To this was added the hydrazinocurdlan-containing mixture mentioned above. Then, 0.82 g of sodium cyanoborohydride was added, and the reaction was carried out in the same manner as in Example 1 to give intramolecularly crosslinked curdlan as a precipitate. This was collected by filtration and thoroughly washed with ethanol to give intramolecularly crosslinked, factor G-free curdlan with a single helix conformation. This was treated in the same manner as in Example 1 for acetylation of unreacted amino groups and for purification, to give intramolecularly crosslinked curdlan of the invention with a single helix conformation.

EXAMPLE 3

2,3,4-Trihydroxyadipodialdehyde-crosslinked hydrazinocurdlan

To 1 g of the hydrazinocurdlan prepared as described in Example 1 was added 1.0 ml of phosphate-buffered physiological saline containing 3 μg/ml of a (1→3)-β-D-glucan-recognizing protein in silkworm plasma (hemolymph) as prepared in advance. The mixture was stirred and then allowed to sand at room temperature for 30 minutes. To this was added 200 ml of 0.1M phosphate buffer (pH 8.0) containing 1% of 2,3,4-trihydroxyadipodialdehyde. The mixture was allowed to stand at room temperature for 2 hours with stirring. Then, 2.5 g of dimethylamine-borane was added thereto and intramolecular crosslinking was effected by stirring at 40° C. for 4 hours. After the reation, ethanol was added to a concentration of 70% to thereby cause precipitation of intramolecularly crosslinked curdlan. The precipitate was collected and thoroughly washed with 70% ethanol.

The thus-obtained, receptor-free, intramolecularly crosslinked curdlan with a single helix conformation was suspended in 0.5 ml of 0.2M aqueous sodium acetate, 0.25 ml of acetic anhydride was added, the mixture was stirred for 30 minutes with cooling at 0° C., 0.25 ml of acetic anhydride was further added, and stirring was continued at room temperature for 30 minutes, for acetylation of unreacted amino groups.

After washing of the product with water, 0.1M aqueous sodium hydroxide, water and phosphate-buffered physiological saline were added, the mixture was thoroughly stirred and then ethanol was added to a concentration of 70% to thereby cause precipitation. This precipitation procedure was repeated to give intramolecularly crosslinked curdlan of the invention with a single helix conformation.

EXAMPLE 4

Dodecamethylenediamine-crosslinked aldehyde schizophyllan

To 5 g of schizophyllan obtained by cultivation of *Schiziphyllum commune* were added 40 ml of water, 17 ml of 2M aqueous sodium hydroxide and 3 ml of epichlorohydrin in that order, and the mixture was stirred at 30° C. for 30 minutes for effecting the reaction. Then, acetone was added to a concentration of 80% relative to water to give a precipitate of epoxy-containing schizophyllan, which was thoroughly washed with 80% aqueous acetone.

To 1 volume of the thus-obtained epoxy-containing schizophyllan was added 2.5 volumes of 80% hydrazine hydrate, and the reaction was carried out at 40° C. for 2 hours with stirring. Then, hydrazinoschizophyllan was precipitated by adding acetone to a concentration of 80%. The precipitate was dissolved in 3 ml of a 40% aqueous solution of glyoxal, 4.1 g of sodium caynoborohydride, and the reaction was conducted at 40° C. for 4 hours with stirring to give aldehyde schizophyllan. This was precipitated by adding acetone to a concentration of 80%, washed with 80% aqueous acetone, dried, then dissolved in DMSO to a concentration of 1% and lyophilized.

The thus-obtained aldehyde schizophyllan was dissolved in 5 ml of a solution of 100 mM of N-acetyl-L-tryptophan in 0.2M aqueous dipotassium hydrogen phosphate, and the solution was allowed to stand at room temperature for 30 minutes.

A solution of 50 g of polyvinylpyrrolidone, 10 g of dodecamethylene diamine and 4.8 g of trimethylamine-borane in 350 ml of 0.2M aqueous dipotassium hydrogen phosphate was added to the above-mentioned aldehyde schizophyllan solution, and the mixture was stirred overnight at 40° C. for intramolecular crosslinking.

To the thus-obtained solution containing intramolecularly crosslinked schizophyllan with a single helix conformation was added ethanol to a concentration of 70% by weight, whereby said crosslinked schizophyllan was precipitated. The precipitate was thoroughly washed with 70% ethanol water and then dissolved in 0.1M phosphate buffer (pH 8), tris(hydroxymethyl)aminomethane was added to the solution with stirring to a concentration of 0.1M. The resultant mixture was stirred at room temperature for 30 minutes for blocking free aldehyde groups.

Acetone was added to the reaction mixture to a concentration of 80% and the resultant precipitate was collected by filtration. This precipitate was dissolved alternatingly and repeatedly in water and phosphate-buffered physiological saline, each time followed by precipitation by addition of acetone, as mentioned above. Finally, the precipitate was thoroughly washed with 80% aqueous acetone, then dissolved in water and lyophilized to give intramolecularly crosslinked schizophyllan of the invention with a single helix conformation.

EXAMPLE 5

Pimelic acid-crosslinked hydrazinoschizophyllan

The hydrazinoschizophyllan obtained in Example 4 was dissolved in DMSO to give a 1% solution. This was lyophilized. To 5 g of the lyophilizate were added 5.0 ml of phosphate-buffered physiological saline containing 30 μg/ml of a horseshoe crab amebocyte lysate factor G fraction prepared in advance and 100 ml of 0.01M acetate buffer (pH 4.7), the mixture was stirred until it became homogeneous, and 2 g of polyethylene glycol with an average molecular weight of 50,000 was further added.

Then, a solution of 24 g of potassium pimelate in 200 ml of water was added, the pH was again adjusted to 4.7, and a solution of 35.7 g of 1-ethyl-3-(3-dimethylaminopropyl)carbodiimde in 100 ml of water was added dropwise with stirring at room temperature to thereby effect the reaction. While maintaining the pH at 4.7, the reaction mixture was stirred gently at room temperature for 48 hours to complete the intramolecular crosslinking.

Acetone was added to the thus-obtained, intramolecularly crosslinked schizophyllan-containing, aqueous solution to a concentration of 80% relative to water, for precipitation of said crosslinked schizophyllan. The precipitate was washed with 80% aqueous acetone and then dissolved in 5 ml of 0.2M aqueous sodium acetate, 2.5 ml of acetic anhydride was added, the mixture was stirred at 0° C. for 30 minutes, 2.5 ml of acetic anhydride was further added, and the mixture was stirred at room temperature for 30 minutes, for acetylation of unreacted amino groups.

Acetone was added to the reaction mixture to a concentration of 80% relative to water, whereby acetylated crosslinked schizophyllan precipitated. The precipitate was washed with 80% aqueous acetone. This was dissolved alternatingly and repeatedly in water, 0.1M aqueous sodium hydroxide, water and phosphate-buffered physiological saline succesively in this order, each time followed by precipitation by adding acetone respectively, as mentioned above. Finally, the precipitate was washed with 80% aqueous acetone to give intramolecularly crosslinked schizophyllan of the invention with a single helix conformation.

EXAMPLE 6

2,3,4-Trihydroxyadipodihydrazide-crosslinked aldehyde schizophyllan

One gram of schizophyllan was dissolved in 100 ml of 0.05M sodium acetate buffer (pH 4.5) containing 1% of sodium periodate and the reaction was conducted at room temperature for 4 hours. Then, 3 volumes of ethanol was added to cause precipitation of aldehyde schizophyllan. The precipitate was dissolved in DMSO and lyophilized. To this was added 1.0 ml of a 10 µg/ml suspension of human lymphocyte zymosan receptor in phosphate-buffered physiological saline. The mixture was allowed to stand at 37° C. for 10 minutes, then a solution of 5 g of polyethylene glycol with an average molecular weight of 100,000 in 5 ml of 0.2M aqueous dipotassium hydrogen phosphate, and the mixture was stirred for blending.

To this was added a mixture prepared from 240 mg of 2,3,4-trihydroxy adipodihydrazide, 26 mg of sodium cyanoborohydride and 0.1 ml of 0.2M aqueous dipotassium hydrogen phosphate, and the reaction was conducted at 37° C. for 48 hours for intramolecular crosslinking. After completion of the reaction, 5 g of ethanolamine was added and the reaction was effected at 40° C. for 30 minutes for blocking free aldehyde groups. Then, 200 ml of water was added, an ion exchange resin, DEAE-Cellulose (OH), was further added, and the mixture was stirred for allowing the human lymphocyte zymosan receptor to be adsorbed on the resin. After filtration, 3 volumes of ethanol was added to the filtrate, and the resultant precipitate was recovered to give intramolecularly crosslinked schizophyllan of the invention with a single helix conformation.

EXAMPLE 7

Glutardialdehyde-crosslinked hydrazinoschizophyllan

To 1 g of the aldehyde schizophyllan obtained in Example 6 were added 0.4 g of adipodihydrazide and 40 mg of sodium cyanoborohydride and the reaction was carried out at 40° C. for 10 hours to give hydrazinoschizophyllan. This was precipitated by adding 3 volumes of ethanol to the reaction mixture.

This precipitate was dissolved in DMSO, then lyophilized, and dissolved in 5 ml of 0.1M phosphate buffer (pH 8.5), 1 g of L-tryptophan was added, and 5 volumes of a 80% aqueous solution of polyethylene glycol with an average molecular weight of 500,000 was added. To this mixture were further added 5 ml of a 25% aqueous solution of glutardialdehyde and 410 mg of sodium cyanoborohydride, and intramolecular crosslinking was effected by reacting at 37° C. for 48 hours with stirring.

Then, 3 volumes of ethanol was added for precipitating intramolecularly crosslinked schizophyllan. The precipitate was dissolved in 0.5 ml of 0.2M aqueous sodium acetate, the solution was cooled to 0° C., 0.25 ml of acetic anhydride was added and, after 30 minutes of stirring, 0.25 ml of acetic anhydride was further added at room temperature, followed by 30 minutes of stirring. After acetylation of unreacted amino groups in that manner, 3 volumes of ethanol was added. The thus-obtained precipitate was dissolved in 0.1M aqueous sodium hydroxide, followed by precipitation in the same manner as mentioned above, dissolution in distilled water, neutralization and precipitation. Repetitions of these operations gave glutaraldehyde-crosslinked hydrazinoschizophyllan of the invention.

EXAMPLE 8

Hexamethylenedihydrazine-crosslinked carboxymethylated curdlan

Ten grams of the same curdlan as used in Example 1 was dissolved in 100 ml of 5M aqueous sodium hydroxide in a nitrogen atmosphere at 0° C. Separately, 23.6 g of monochloroacetic acid was dissolved in 20 ml of water. This aqueous solution of monochloroacetic acid was added dropwise to the above curdlan solution with stirring and the resultant mixture was kept stirred at 60°–65° C. for 2 hours. The resultant gel-like matter was added to 5 volumes of ethanol, the mixture was stirred vigorously and the resultant fine powder was collected by filtration. The solid was thoroughly washed with 70% aqueous ethanol, then washed in sequence with ethanol and ethyl ether, and dried. The thus-purified fine powder was dissolved in 700 ml of water, the solution was neutralized with 1M aqueous acetic acid, then stirred with 40 g of active carbon at room temperature for 1 hour and filtered. The filtrate was concentrated to 100 ml under reduced pressure and 300 ml of ethanol was added thereto. A precipitate formed. This was collected by filtration, washed in sequence with ethanol and ethyl ether, and dried over concentrated sulfuric acid to give 11.4 g of partially carboxymethylated curdlan with a substitution degree of 0.63 per glucose residue.

The thus-obtained partially carboxymethylated curdlan was dissolved in DMSO to a concentration of about 1% and lyophilized. To 1 g of the lyophilizate were added 1.0 ml of phosphate-buffered physiological saline containing 30 µg/ml of a horseshoe crab amebocyte lysate factor G fraction and 100 ml of 0.01M acetate buffer, and the mixture was stirred until it became homogenous. Then, 10 g of polyvinylpyrrolidone was added, 50 ml of an aqueous solution containing 6 g of hexamethylenedihydrazide was added and, further, 20 ml of an aqueous solution containing 8 g of 1-ethyl-3-(3-dimethylaminopropyl)carbodiimde was added dropwise to the system with stirring at room temperature. The reaction mixture was gently stirred continuedly at room temperature for 48 hours while the pH was adjusted to 4.7. The intramolecular crosslinking reaction was thus driven to completion.

Three volumes of ethanol was added to the reaction mixture and the resultant precipitate was purified by repeating precipitation as in Example 6 to give intramolecularly crosslinked, carboxymethylated curdlan of the invention with a single helix conformation.

EXAMPLE 9

Glutardialdehyde-crosslinked hydrazino yeast glucan

Yeast glucan of a commercial grade (Sigma) was thoroughly washed with water and the solvent was removed by suction filtration, whereby oligosaccharides and other impurities were eliminated. To 5 g of this purified yeast glucan were added 30 ml of water, 13 ml of 2M aqueous sodium hydroxide and 1 ml of epichlorohydrin in that order with stirring. The mixture was stirred at 40° C. for 30 minutes for effecting the reaction and then the solid matter was thoroughly washed with water to give an epoxy derivative. This was suspended in a half volume of water. To this suspension was added an equal volume of 80% hydrazine hydrate, the mixture was stirred at 40° C. for 1 hour for effecting the reaction, and the solid was thoroughly washed with water, dried, dissolved in DMSO to a concentration of 5% and then lyophilized.

To 1 g of the thus-obtained yeast glucan lyophilizate with hydrazino groups introduced therein was added 1.0 ml of phosphate-buffered physiological saline containing 3 µg/ml of a horseshoe crab amebocyte lysate factor G fraction prepared in advance. The mixture was stirred until it became homogeneous, and then allowed to stand at room temperature for 30 minutes.

A solution of 2 g of polyethylene glycol with a average molecular weight of 50,000 in 10 ml of water was added to 1 ml of a 25% aqueous solution of glutardialdehyde to give a homogeneous aqueous solution. This was added to the hydrazino-yeast glucan-containing mixture mentioned above. Then, 0.15 g of sodium cyanoborohydride was added and the mixture was stirred at 40° C. for 4 hours for effecting the intramolecular crosslinking reaction. After completion of the reaction, ethanol was added to a concentration of 70%, and the resultant mixture was allowed to stand for causing the crosslinked yeast glucan to precipitate. The mixture was filtered and the precipitate was thoroughly washed with ethanol.

The thus-obtained, now factor G-free, intramolecularly crosslinked yeast glucan with a single helix conformation was suspended in 0.5 ml of 0.2M aqueous sodium acetate, 0.25 ml of acetic anhydride was added, the mixture was stirred for 30 minutes with cooling at 0° C., 0.25 ml of acetic anhydride was further added and stirring was continued at room temperature for 30 minutes, for acetylating unreacted amino groups. The product was washed with water, further washed thoroughly with 0.1M aqueous sodium hydroxyde and water, collected by filtration and dried to give intramolecularly crosslinked yeast glucan of the invention with a single helix conformation.

EXAMPLE 10

Glutardialdehyde-crosslinked hydrazinolentinan

Lentinan was prepared by the method of Chihara et al. [Chihara, G. et al., Cancer Research, 30, 2776–2781 (1970)] as follows. Eight kilograms of raw shiitake mushroom (fruit bodies of Lentinus edodes) was washed with cold water, mashed in a mixter, and extracted with a total of 40 liters of boiling water for 8 hours. The suspension was filtered through a chesse cloth, and the filtrate was concentrated under reduced pressure until it became somewhat turbid. To the concentrate was added an equal volume of ethanol. The resultant precipitate was collected (12.8 g) and 10 g thereof was dissolved in water (4,400 ml). To the solution was added 0.2M cetyltrimethylammonium hydroxide (CTA-OH) until precipitation was complete. The precipitate obtained was collected by 5 minutes of centrifugation at 9,000 rpm, and subjected to 5 minutes of extraction with 240 ml of 20% acetic acid at 0° C. and then to 3 minutes of extraction with 50% acetic acid at 0° C. The insoluble matter was dissolved in 400 ml of 6% aqueous sodium hydroxide, and 3 volumes of ethanol was added to the solution for causing precipitation. The precipitate was deproteinized by the method of Sevag [Whistler, R. L. (ed.), Methods in Carbohydrate Chemistry, 5, 5–6 (1965), Academic Press, Inc., New York] using chloroform and 1-butanol, precipitated with 3 volumes of ethanol, washed with methanol and ether, and dried under reduced pressure over calcium oxide at room temperature to give 6.2 g of lentinan.

To 5 g of the thus-obtained lentinan were added 30 ml of water, 13 ml of 2M aqueous sodium hydroxide and 1.5 ml of epichlorohydrin in that order with stirring. The mixture was stirred at 40° C. for 30 minutes for effecting the reaction, and the solid matter was then thoroughly washed with a mixture of acetone (80%) and water (20%) to give an epoxy derivative. This was suspended in a half volume of water. To this suspension was added an equal volume of 80% hydrazine hydrate, the reaction was carried out at 40° C. for 1 hour with stirring, and the solid was thoroughly washed with the same acetone-water mixture as mentioned above, dried, dissolved in DMSO to a concentration of 5% and then lyophilized.

To 1 g of the thus-lyophilized lentinan with hydrazino groups introduced therein was added 1.0 ml of phosphate-buffered physiological saline containing 3 µg/ml of a horseshoe crab amebocyte lysate factor G fraction prepared in advance. The mixture was stirred until it became homogeneous, and then allowed to stand at room temperature for 30 minutes.

A solution of 2 g of polyethylene glycol with an average molecular weight of 50,000 in 10 ml of water was added to 1 ml of a 25% aqueous solution of glutardialdehyde to give a homogeneous aqueous solution. This was added to the hydrazinolentinan-containing mixture mentioned above. Then, 125 mg of sodium cyanoborohydride was added, and the intramolecular crosslinking reaction was effected by continuing stirring at 40° C. for 4 hours. After completion of the reaction, ethanol was added to a concentration of 70% and the resultant mixture was allowed to stand for precipitation of crosslinked lentinan. The mixture was filtered and the precipitate was thoroughly washed with ethanol.

The thus-obtained, now factor G-free, intramolecularly crosslinked lentinan with a single helix conformation was suspended in 0.5 ml of 0.2M aqueous sodium acetate, 0.25 ml of acetic anhydric was added, the mixture was stirred for 30 minutes with cooling at 0° C., 0.25 ml of acetic anhydride was then further added, and stirring was continued at room temperature for 30 minutes, for acetylating unreacted amino groups. The solid product was washed with water, further thoroughly washed with 0.1M aqueous sodium hydroxide and water, recovered by filtration, and dried to give intramolecularly crosslinked lentinan of the invention with a single helix conformation.

Test Example

The crosslinked, single helix conformation glucans obtained in Examples 1–10 were tested for single helix conformation content, factor G activating ability and tumor inhibition rate, as mentioned below. For comparison, uncrosslinked, single helix conformation schizophyllan activated with alkali was evaluated in the same manner. They were also evaluated for long period stability by comparing the values immediately after synthesis with the values after 1 month.

(1) Single helix conformation content

Each sample was deprived of water by lyophilization and then maintained in saturated water vapor, and the hydrated solid sample obtained was subjected to high-resolution $^{13}$C-NMR spectrometry. The single helix conformation content in the (1→3)-β-D-glucan in the sample was calculated by comparing the chemical shift peak heights for each carbon atom with the peak heights of the chemical shifts shown in Table 1 for other higher-order structure carbon atoms.

TABLE 1

| Higher order | Chemical shift (ppm) | | |
|---|---|---|---|
| | C-2 | C-3 | C-5 |
| Single helix | 73.8 ± 0.3 | 87.3 ± 0.3 | 75.8 ± 0.3 |
| Triple helix | 74.3 ± 0.3 | 86.5 ± 0.3 | 77.5 ± 0.3 |
| Random coil | 73.0 ± 0.3 | 91.0 ± 0.3 | 75.6 ± 0.3 |

The single helix conformation contents thus obtained from the chemical shifts of C-2, C-3 and C-5 and the respective peak heights are shown in Table 2.

TABLE 2

| | | Single helix conformation | | | | |
|---|---|---|---|---|---|---|
| | Sample | Content in hydrated | % Retention | % Retention of factor G | % Tumor inhibition*¹ | |
| Example | Substance name | solid sample (%) | After one month | activating ability After one month | Initial | After one month |
| 1 | Glutardialdehyde-crosslinked hydrazinocurdlan (no receptor added) | 70 | 60 | 10 | 98.0 | 70.0 |
| 2 | Glutardialdehyde-crosslinked hydrazinocurdlan | 65 | 70 | 20 | 98.2 | 91.1 |
| 3 | 2,3,4-trihydroxy-adipodialdehyde-crosslinked hydrazinocurdlan | 70 | 80 | 20 | 100 | 92.1 |
| 4 | Dodecamethylene-diamine-crosslinked aldehyde schizophyllan | 75 | 100 | 100 | 100 | 98.4 |
| 5 | Pimelic acid-crosslinked hydrazino-schizophyllan | 55 | 60 | 10 | 95.3 | 65.6 |
| 6 | 2,3,4-trihydroxy-adipodihydrazide-crosslinked aldehyde schizophyllan | 70 | 90 | 30 | 100 | 96.1 |
| 7 | Glutardialdehyde-crosslinked hydrazino-schizophyllan | 70 | 80 | 25 | 100 | 95.0 |
| 8 | Hexamethylenedi-hydrazine-crosslinked carboxy-methylated curdlan | 60 | 70 | 10 | 98.2 | 75.3 |
| 9 | Glutardialdehyde-crosslinked hydrazino yeast glucan | 23 | 53 | 20 | 90.0 | 73.0 |
| 10 | Glutardialdehyde-crosslinked hydrazinolentinan | 35 | 52 | 20 | 96.0 | 80.0 |
| — | Non-crosslinked activated single helix schizophyllan (for comparison)*² | 60 | 10 | 0.001 | 98.0 | 15.5 |

Notes:
*¹Mean tumor weight in untreated control group:
Initial value 14.45 ± 4.95 g
After 1 month 13.86 ± 5.15 g
*²Prepared from a commercial grade of schizophyllan by alkali treatment.

Furthermore, aqueous solutions or suspensions were stored in aseptic condition at 4° C. for 1 month and then tested for single helix conformation content in the same manner. The data obtained were compared with the initial values and the rates of retention of the respective single helix conformations contained were calculated. The results obtained are shown in Table 2. The uncrosslinked, single helix conformation schizophyllan, when subjected to solid-phase $^{13}$C-NMR spectrometry immediately after formation of said conformation, gave a single helix conformation content of 60% but, after one-month storage, the content of said structure was only 6% (10% retention). This is due to advanced transformation from the single helix conformation to other higher-order structures.

(2) Factor G activating ability

For each sample to be tested, a reaction mixture (200 μl) containing the sample, water and the ingredients mentioned below was prepared.

| Sample | 50 μl |
|---|---|
| Horseshoe crab lysate proclotting enzyme fraction ($A_{280}$ = 2.5) | 30 μl |
| Horseshoe crab lysate factor G fraction ($A_{280}$ = 0.9) | 20 μl |
| Tris-hydrochloride buffer (pH 8.0) | 20 μmol |
| Magnesium chloride | 20 μmol |
| Boc—Leu—Gly—Arg—pNA | 0.13 μmol |

This reaction mixture was incubated at 37° C. for 30 minutes and, then, p-nitroaniline (pNA) liberated was quantitated. Thus, to the sample after incubation were added 0.5 ml each of 0.04% sodium nitrite (solution in 0.48M hydrochloric acid), 0.3% ammonium sulfamate and 0.07% N-1-naphthylethylenediamine dihydrichloride in that order for causing a change in color tone due to diazo coupling, and the absorbance at 545 nm ($A_{545}$) was determined.

This measurement was performed for an aqueous solution or suspension of each substance immediately after synthesis thereof. The same measurement was also performed after one month storage of the sample at 4° C., the minimum concentration (C, g/ml) at which the absorbance at 545 nm amounted to 0.1 was determined, and the factor G activating ability was expressed in terms of −log C (g/ml) value. By comparing this value with the initial value, the rate of retention of factor G activating ability was calculated. The results thus obtained are shown in Table 2.

While the initial factor G activating ability expressed in terms of −log C (g/ml) was 12 for the uncrosslinked, activated schizophyllan (Comparative Example), the value for the intramolecularly crosslinked curdlan obtained in Example 1 was 11, indicating that the factor G activating ability of the crosslinked curdlan was superior, namely 10-times higher.

(3) Tumor inhibition rate

Sarcoma 180 cells (5×10$^6$ cells) were transplanted subcutaneously into the groin of each of 6-week-old CLJ-ICR female mice weighing about 25 g. The intramolecularly crosslinked, single helix conformation (1→3)-β-D-glucans of the invention as obtained in Examples 1–10 and the uncrosslinked, single helix conformation schizophyllan of Comparative Example were respectively administered to the mice at 24 hours after transplantation (day 1) and thereafter once daily on days 1–5 and 7–11 (10 times in total). Thus, each sample was comminuted in a mortar, suspended or dissolved in physiological saline for injection, sterilized in an autoclave at 121° C. for 20 minutes, and then intraperitoneally administered. In a control group, no glucan was given to mice.

On day 13, tumor nodules were excised and weighed, and their weights were compared with the tumor weight in the untreated control group for calculating tumor inhibition rates.

In the above test, sample solutions or suspensions were administered immediately after preparation on one hand and, on the other, the solutions or suspensions were administered after one month storage at 4° C. The results obtained in both modes of testing are shown in Table 2.

As is evident from Table 2, the aqueous solutions or suspensions of the intramolecularly crosslinked glucans of the invention, even after one month storage at 4° C., showed satisfactorily retained factor G activating ability levels and tumor inhibition rates as a result of stabilization of their single helix conformation by intramolecular crosslinking. Thus, under these conditions, the intramolecularly crosslinked (1→3)-β-D-glucans showed a factor G activating ability retention of at least 10%, the highest retention being 100% in one case. This is extremely high as compared with the value 0.001% in the case of uncrosslinked, single helix conformation schizophyllan. The rate of retention of factor G activating ability after one month is lower than the rate of retention of single helix conformation content. This is because the single helix conformation moiety should have a certain minimum length for the activation of factor G; the longer such moiety is, the stronger the factor G activating ability is. Furthermore, even after one month storage, the tumor inhibition rates were not less than 65% and, in an extreme case, exceeded 98%, exhibiting a marked contrast to the value of 15.5% for uncrosslinked, single helix conformation schizophyllan after one month storage.

While the invention has been described in detail and with reference to specific embodiments thereof, it will be appaent to one skilled in the art that various changes and modifications can be made therein without departing from the spirit and scope thereof.

What is claimed is:

1. A method of producing an islolated (1→3)-β-D-glucan that is intramolecularly crosslinked to have a stable single helix conformation which method comprises:

(a) forming a single helix conformation of an isolated (1→3)-β-D-glucan having at least 20 D-glucoside units having hydroxyl groups, wherein the hydrogen atoms of at least part of the hydroxyl groups are substituted with functional groups that are reactive with a bifunctional crosslinking agent, and (b) intramolecularly crosslinking the glucan between the functional groups described in said step (a) by using said crosslinking agent in the presence of polyethylene glycol, polyvinyl alcohol, polyvinylpyrrolidone or water-soluble copolymers that contain at least one of polyethylene glycol, polyvinyl alcohol, or polyvinylpyrrolidone as principal constituents, which are not reactive with the functional groups described in said step (a) so as to prevent intermolecular crosslinking.

2. A method of producing an isolated (1→3)-β-D-glucan that is intramolecularly crosslinked to have a stable single helix conformation which method comprises:

(a) forming a single helix conformation of an isolated (1→3)-β-D-glucan having at least 20 D-glucoside units having hydroxyl groups wherein the hydrogen atoms of at least part of the hydroxyl groups are substituted with functional groups, that are reactive with a bifunctional crosslinking agent, and (b) binding the glucan having a single helix conformation to a receptor for (1→3)-β-D-glucan, wherein said receptor is selected from the group consisting of horseshoe crab amebocyte lysate, factor G from horseshoe crab amebocyte lysate, arthropod phenol oxidase precursor, zymosan receptor from human lymphocytes, carbohydrate-receptive amino acids and tryptophan-containing peptides, (c) intramolecularly crosslinking the glucan between the functional groups described in said step (a) by using said crosslinking agent in the presence of polyethylene glycol, polyvinyl alcohol, polyvinylpyrrolidone or water-soluble copolymers that contain at least one of polyethylene glycol, polyvinyl alcohol, or polyvinylpyrrolidone as principal constituents, which are not reactive with the functional groups described in said step (a) so as to prevent intermolecular crosslinking, and (d) eliminating said receptor.

3. An isolated (1→3)-β-D-glucan that is intramolecularly crosslinked to have a stable single helix conformation, wherein said glucan that is intramolecularly crosslinked has the following characteristics:

(i) a single helix conformation content of at least 20% as determined in a hydrated solid state;

(ii) a single helix conformation retention of at least 50% as determined after one month storage at 4° C. in the form of an aqueous solution or suspension;

(iii) retains horseshoe crab factor G activating ability, host-mediated antitumor activity, or both horseshoe crab factor G activating ability and host-mediated antitumor activity; and (iv) has been intramolecularly crosslinked so as to prevent intermolecular crosslinking.

4. A pharmaceutical composition comprising an isolated (1→3)-β-D-glucan that is intramolecularly crosslinked to have a stable single helix conformation and a pharmaceutically acceptable carrier, wherein said glucan that is intramolecularly crosslinked has the following characteristics:

(i) a single helix conformation content of at least 20% as determined in a hydrated solid state;

(ii) a single helix conformation retention of at least 50% as determined after one month storage at 4° C. in the form of an aqueous solution or suspension;

(iii) retains horseshoe crab factor G activating ability, host-mediated antitumor activity, or both horseshoe crab factor G activating ability and host-mediated antitumor activity; and (iv) has been intramolecularly crosslinked so as to prevent intermolecular crosslinking.

5. The isolated (1→3)-β-D-glucan that is intramolecularly crosslinked to have a stable single helix conformation according to claim 3 which is produced by a process comprising:

(a) forming a single helix conformation of a (1→3)-β-D-glucan having at least 20 D-glucoside units having hydroxyl groups, wherein the hydrogen atoms of at least part of the hydroxyl groups are substituted with functional groups that are reactive with a bifunctional crosslinking agent, and (b) intramolecularly crosslinking the glucan between the functional groups described in said step (a) by using said crosslinking agent in the presence of polyethylene glycol, polyvinyl alcohol, polyvinylpyrrolidone or water-soluble copolymers that contain at least one of polyethylene glycol, polyvinyl alcohol, or polyvinylpyrrolidone as principal constituents and which are not reactive with the functional groups described in said step (a) so as to prevent intermolecular crosslinking.

6. The isolated (1→3)-β-D-glucan that is intramolecularly crosslinked to have a stable single helix conformation according to claim 3 which is produced by a process comprising:

(a) forming a single helix conformation of a (1→3)-β-D-glucan having at least 20 D-glucoside units having hydroxyl groups, wherein the hydrogen atoms of at least part of the hydroxyl groups are substituted with functional groups that are reactive with a bifunctional crosslinking agent, (b) binding the glucan having a single helix conformation to a receptor for said (1→3)-β-D-glucan, wherein said receptor is selected from the group consisting of horseshoe crab amebocyte lysate, factor G from horseshoe crab amebocyte lysate, arthropod phenol oxidase precursor, zymosan receptor from human lymphocytes, carbohydrate-receptive amino acids and tryptophan-containing peptides, (c) intramolecularly crosslinking the glucan between the functional groups described in said step (a) by using said crosslinking agent in the presence of polyethylene glycol, polyvinyl alcohol, polyvinylpyrrolidone or water-soluble copolymers that contain at least one of polyethylene glycol, polyvinyl alcohol, or polyvinylpyrrolidone as principal constituents, which are not reactive with the functional groups described in said step (a) so as to prevent intermolecular crosslinking, and (d) eliminating the receptor.

* * * * *